(12) United States Patent
Shinozuka et al.

(10) Patent No.: US 9,067,376 B2
(45) Date of Patent: Jun. 30, 2015

(54) GREEN HONEYCOMB MOLDING DEFECT EXAMINATION METHOD, GREEN HONEYCOMB STRUCTURE MANUFACTURING METHOD, AND GREEN HONEYCOMB MOLDING DEFECT EXAMINATION DEVICE

(71) Applicant: SUMITOMO CHEMICAL COMPANY, LIMITED, Chuo-ku, Tokyo (JP)

(72) Inventors: Atsuhiko Shinozuka, Niihama (JP); Yukihito Tokuoka, Niihama (JP); Kazuya Tsuchimoto, Niihama (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/328,185

(22) Filed: Jul. 10, 2014

(65) Prior Publication Data

US 2014/0319714 A1 Oct. 30, 2014

Related U.S. Application Data

(63) Continuation of application No. PCT/JP2012/084134, filed on Dec. 28, 2012.

(30) Foreign Application Priority Data

Jan. 12, 2012 (JP) ................................ 2012-004140

(51) Int. Cl.
*B29D 99/00* (2010.01)
*B01D 39/20* (2006.01)
(Continued)

(52) U.S. Cl.
CPC ............ *B29D 99/0089* (2013.01); *B01D 39/20* (2013.01); *F01N 3/00* (2013.01); *G01M 3/00* (2013.01); *G01N 15/08* (2013.01); *G01M 3/38* (2013.01)

(58) Field of Classification Search
CPC ....... G01N 21/41; G01N 21/43; G01N 21/45; G01N 21/47; G01N 21/49; G01N 21/53; G01N 21/95; G01M 3/02
USPC ............................................. 356/237.1–237.6
See application file for complete search history.

(56) References Cited

U.S. PATENT DOCUMENTS

2003/0112437 A1 6/2003 Enomoto et al.
2006/0151926 A1 7/2006 Zoeller, III
(Continued)

FOREIGN PATENT DOCUMENTS

EP 2 233 908 A2 9/2010
JP 06-026323 A 2/1994
(Continued)

OTHER PUBLICATIONS

International Preliminary Report on Patentability and Notification for PCT/JP2012/084134 dated Jul. 15, 2014.
(Continued)

*Primary Examiner* — Rebecca C Bryant
(74) *Attorney, Agent, or Firm* — Sughrue Mion, PLLC (57) ABSTRACT

Disclosed is a method of examining defects in a green honeycomb molding having partition walls which form a plurality of flow channels extending in parallel with one another, and sealing portions which close the upper ends of some of the plurality of flow channels and the lower ends of the rest flow channels. The method includes a step of applying pressure to the lower ends of the plurality of flow channels using gas, and a step of visualizing the distribution of gas refractive indexes near the upper ends of the plurality of flow channels.

13 Claims, 8 Drawing Sheets

(51) Int. Cl.
*F01N 3/00* (2006.01)
*G01M 3/00* (2006.01)
*G01N 15/08* (2006.01)
*G01M 3/38* (2006.01)

(56) References Cited

U.S. PATENT DOCUMENTS

| | | |
|---|---|---|
| 2007/0022724 A1 | 2/2007 | Gargano et al. |
| 2008/0205596 A1 | 8/2008 | Kato |
| 2008/0225302 A1 | 9/2008 | Nagatoshi et al. |
| 2010/0201983 A1 | 8/2010 | Hatano et al. |

FOREIGN PATENT DOCUMENTS

| | | |
|---|---|---|
| JP | 2002-357562 A | 12/2002 |
| JP | 2005-283547 A | 10/2005 |
| JP | 2008-139184 A | 6/2008 |
| JP | 2009-503508 A | 1/2009 |
| JP | 2010-230460 A | 10/2010 |
| WO | 2009/028709 A1 | 3/2009 |
| WO | 2011/142268 A1 | 11/2011 |

OTHER PUBLICATIONS

Written Opinion for PCT/JP2012/084134 dated Mar. 19, 2014.
International Search Report for PCT/JP2012/084134 dated Mar. 19, 2013.

GREEN HONEYCOMB MOLDING DEFECT EXAMINATION METHOD, GREEN HONEYCOMB STRUCTURE MANUFACTURING METHOD, AND GREEN HONEYCOMB MOLDING DEFECT EXAMINATION DEVICE

TECHNICAL FIELD

An embodiment of the invention relates to a green honeycomb molding defect examination method, a green honeycomb structure manufacturing method, and a green honeycomb molding defect examination device.

BACKGROUND ART

A method of examining defects in a green honeycomb molding, which is a molding before baking of a so-called honeycomb filter, has been heretofore known. For example, Patent Literatures 1 and 2 disclose that a gas flow including particulates is provided to the entrance end surface of a green honeycomb molding, a gas flow emerging out of the exit end surface of the green honeycomb molding flows through a transmissive member, such as a screen, and particulates emerging out of the transmissive member is illuminated using a light source.

CITATION LIST

Patent Literature

[Patent Literature 1] PCT Japanese Translation Patent Publication No. 2009-503508
[Patent Literature 2] Japanese Unexamined Patent Application Publication No. 2002-357562

SUMMARY OF INVENTION

Technical Problem

However, in the method of the related art, since particulates remain in the green honeycomb molding, it is necessary to remove particulates after examination, and the method becomes complicated.

An embodiment of the invention has been accomplished in consideration of the above-described problem, and an object of the invention is to provide a method and a device capable of easily examining defects in a green honeycomb molding, and a method of manufacturing a green honeycomb structure using the same.

Solution to Problem

According to an embodiment of the invention, there is provided a method of examining defects in a green honeycomb molding having partition walls which form a plurality of flow channels extending in parallel with one another, and sealing portions which close one end of some of the plurality of flow channels and the other end of the rest of the plurality of flow channels. The method includes a step of applying pressure to one end of the plurality of flow channels using gas, a step of acquiring a plurality of first direction images visualizing the distribution of refractive indexes of gas near the other end of the plurality of flow channels from a first direction intersecting the axis of the plurality of flow channels at different times, a step of acquiring a plurality of second direction images visualizing the distribution of refractive indexes of gas near the other end of the plurality of flow channels from a second direction intersecting the axis of the plurality of flow channels and intersecting the first direction at different times, a step of selecting an image having a largest number of jet flows of gas discharged from the other end of the plurality of flow channels of the green honeycomb molding in the plurality of first direction images, a step of selecting an image having a largest number of jet flows of gas discharged from the other end of the plurality of flow channels of the green honeycomb molding in the plurality of second direction images, and a step of acquiring information relating to the positions of the jet flows in the selected two images.

According to another embodiment of the invention, there is provided a device for examining defects in a green honeycomb molding having partition walls which form a plurality of flow channels extending in parallel with one another, and sealing portions which close one end of some of the plurality of flow channels and the other end of the rest of the plurality of flow channels. The device includes a pressure application member which applies pressure to one end of the plurality of flow channels using gas supplied from a gas supply source, a first visualization unit which acquires a plurality of first direction images visualizing the distribution of refractive indexes of gas near the other end of the plurality of flow channels from a first direction intersecting the axis of the plurality of flow channels at different times, a second visualization unit which acquires a plurality of second direction images visualizing the distribution of refractive indexes of gas near the other end of the plurality of flow channels from a second direction intersecting the axis of the plurality of flow channels and intersecting the first direction at different times, a first selection unit which selects an image having a largest number of jet flows of gas discharged from the other end of the plurality of flow channels of the green honeycomb molding in the plurality of first direction images, a second selection unit which selects an image having a largest number of jet flows of gas discharged from the other end of the plurality of flow channels of the green honeycomb molding in the plurality of second direction images, and a position acquisition unit which acquires information relating to the positions of the jet flows in the selected two images.

According to the embodiments of the invention, when there are no defects allowing the flow channels to communicate with one another or no defects of the sealing portions, since either one end or the other end of each flow channel is closed by the sealing portion, gas does not pass through the flow channel and flow out of the other end. In contrast, when the partition walls have defects allowing the flow channel to communicate with each other or the sealing portions of the flow channels have defects, gas for applying the pressure passes through the flow channel and flows out of the other end of the flow channel. Accordingly, the refractive index of leaking gas is different from the refractive index of atmospheric gas near the other end, the distribution of refractive indexes changes, and an image visualizing the change is obtained, thereby detecting the presence/absence or the locations of defects.

Since images visualized from two different directions are acquired, it is easy to specify the positions of defects.

Since an image having a largest number of jet flows is selected from a plurality of images visualized from each direction, there is less influence of temporal fluctuations in jet flows discharged from defective portions, and defective locations can be specified with high precision.

The method according to the embodiment of the invention further includes, when the number of positions where defects in the green honeycomb molding are likely to be present by information acquired in the step of acquiring information relating to the positions of the jet flows in the selected two images is equal to or greater than a predetermined threshold value, a step of acquiring a plurality of third to nth direction images visualizing the distribution of refractive indexes of gas near the other end of the plurality of flow channels from third to n-th directions (where n is an integer equal to or greater than 3) intersecting the axis of the plurality of flow channels, intersecting the first direction and the second direction, and intersecting one another at different times, a step of selecting images having a largest number of jet flows of gas discharged from the other end of the plurality of flow channels of the green honeycomb molding in the third to n-th direction images, and a step of acquiring information relating to the positions of the jet flows in the selected three to n images.

The device according to the embodiment of the invention further includes, when the number of positions where defects in the green honeycomb molding are likely to be present by information acquired by information relating to the positions of the jet flows in the selected two images acquired by the position acquisition unit is equal to or greater than a predetermined threshold value, a third visualization unit to an n-th visualization unit which acquire a plurality of third to n-th direction images visualizing the distribution of refractive indexes of gas near the other end of the plurality of flow channels from third to n-th directions (where n is an integer equal to or greater than 3) intersecting the axis of the plurality of flow channels, intersecting the first direction and the second direction, and intersecting one another at different times, and a third selection unit to an n-th selection unit which select images having a largest number of jet flows of gas discharged from the other end of the plurality of flow channels of the green honeycomb molding in the third to n-th direction images, in which the position acquisition unit acquires information relating to the positions of the jet flows in the selected three to n images.

According to the embodiment of the invention, when it is estimated that the number of positions where defects are likely to be present by information relating to the positions of the jet flows in the two images is equal to or greater than the predetermined threshold value, similarly, the plurality of third to n-th direction images visualizing the distribution of refractive indexes of gas are further acquired from the third to n-th directions at different times, the images having a largest number of jet flows of gas discharged from the other end of the plurality of flow channels in the plurality of third to n-th direction images are selected, and information relating to the positions of the jet flows in the three to n images is acquired. With this, it is possible to acquire information relating to the positions of the jet flows in a larger number of images, and to limit the positions, at which defects are likely to be present, to a smaller number of positions.

The method according to the embodiment of the invention further includes a step of detecting the pressure of the jet flows of gas discharged from the other end of the plurality of flow channels of the green honeycomb molding to acquire information relating to the positions of the jet flows.

The device according to the embodiment of the invention further includes a pressure sensor which detects the pressure of the jet flows of gas discharged from the other end of the plurality of flow channels of the green honeycomb molding, in which the position acquisition unit acquires information relating to the positions of the jet flows by the pressure of the jet flows of gas discharged from the other end of the plurality of flow channels detected by the pressure sensor.

According to the embodiment of the invention, in addition to the above-described configuration, since the pressure of the jet flows of gas discharged from the other end of the plurality of flow channels of the green honeycomb molding is detected to acquire information relating to the positions of the jet flows, it is possible to limit the positions, at which defects are present, with higher precision.

The distribution of refractive indexes may be visualized by one of a shadow graph method, a Mach-Zehnder method, and a schlieren method, and may be detected by the schlieren method.

When the density of atmospheric gas near the other end of the plurality of flow channels is 1 at 0° C., 1 atm, the density of gas for applying the pressure may be in a range of 0.1 to 0.9 or 1.1 to 5.0 at 0° C., 1 atm. With this, a sufficient difference in refractive index is provided between atmospheric gas and leaking gas, whereby it is possible to detect leakage of gas.

Specifically, the pressure may be applied to one end of the plurality of flow channels using gas having a composition different from atmospheric gas near the other end of the plurality of flow channels.

In either a state in which the vicinity of the other end of the plurality of flow channels is in vacuum or a state in which atmospheric gas near the other end of the plurality of flow channels may be gas having a density difference from gas for applying the pressure, gas for applying the pressure is gas of one selected from a group consisting of helium, neon, nitrogen, argon, xenon, krypton, oxygen, and carbon dioxide, mixed gas of two or more of the group, or mixed gas of one or more of the group and air.

The pressure may be applied to one end of the plurality of flow channels using gas at a temperature different from atmospheric gas near the other end of the plurality of flow channels. With this, even when gas having the same composition as atmospheric gas near the other end of the plurality of flow channels is used as gas for applying the pressure, a density difference can be provided to gas, and visualization is possible.

Scales may be arranged within the visual field of the plurality of first direction images and the plurality of second direction images. With this, the locations where gas leaks are more easily specified based on the images, and the positions of defects are easily understood.

The distribution of refractive indexes of gas near the other end of the plurality of flow channels may be visualized from a direction orthogonal to the axis of the plurality of flow channels to acquire the plurality of first direction images and the plurality of second direction images. With this, leakage of gas is easily detected.

The first direction and the second direction may be orthogonal to each other. With this, two-dimensional coordinate information for the locations of leakage is easily obtained, and defective flow channels are easily specified.

The green honeycomb molding may contain an inorganic compound source and a binder.

A method of manufacturing a green honeycomb structure according to still another embodiment of the invention includes a step of recognizing the positions of defects based on the above-described examination method, and a step of repairing the recognized defects.

Accordingly, yield is improved.

Advantageous Effects of Invention

According to the embodiment of the invention, it is possible to easily examine defects in the green honeycomb molding.

DESCRIPTION OF EMBODIMENTS

An embodiment of the invention will be described referring to the drawings. First, a green honeycomb molding 100 to be examined in this embodiment will be described.

Figure 1:
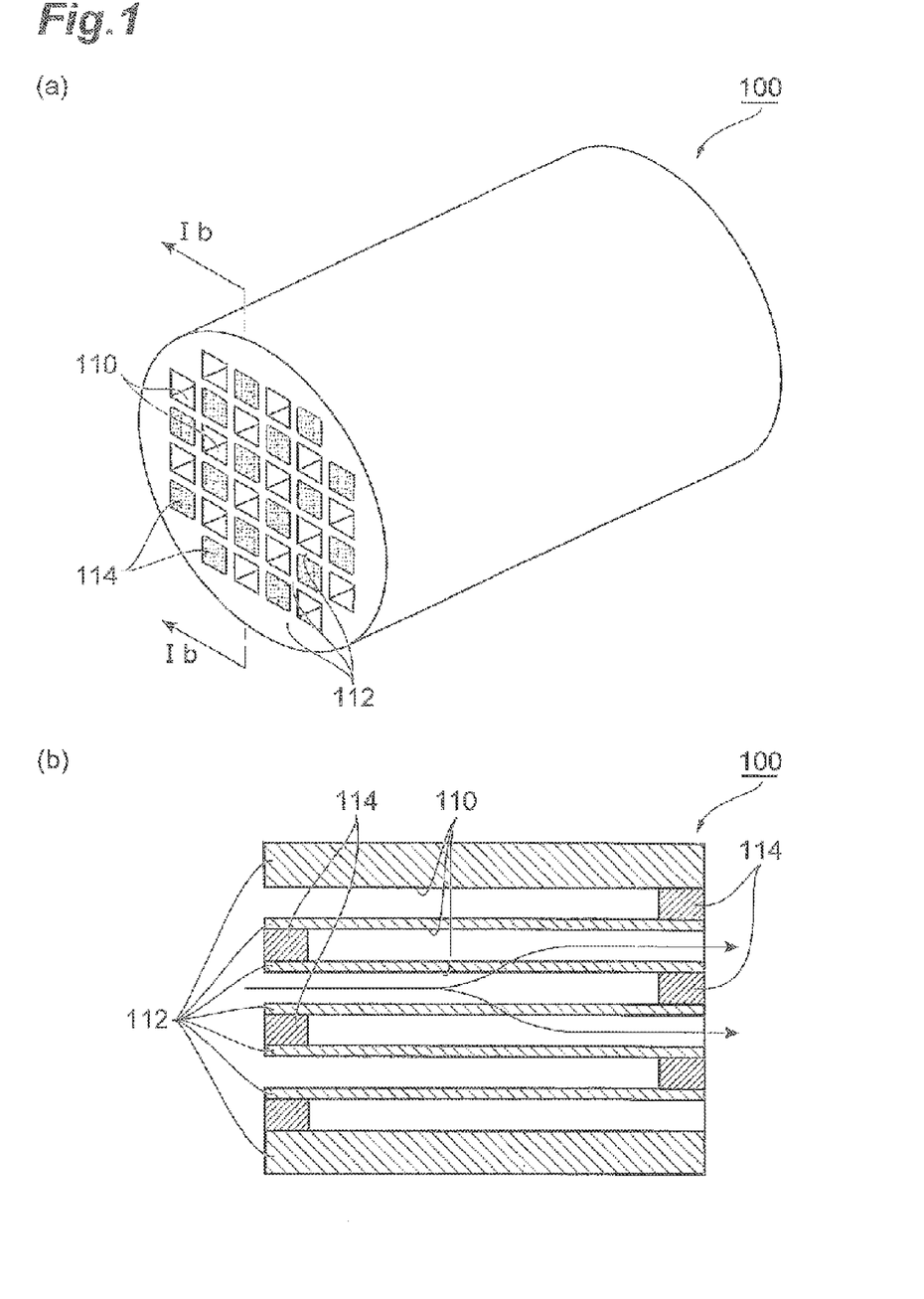
FIG. 1(a) is a perspective view of a green honeycomb molding 100 to be examined.
FIG. 1(b) is a diagram when viewed from the arrow direction of Ib-Ib of FIG. 1(a).

As shown in FIGS. 1(a) and 1(b), the target green honeycomb molding 100 in this embodiment is a columnar body having partition walls 112 which form a plurality of flow channels 110 extending in parallel with one another, and sealing portions 114 which close one end (the left end of FIG. 1(b)) of some of the plurality of flow channels 110 and the other end (the right end of FIG. 1(b)) of the rest of the plurality of flow channels 110.

The length of the direction in which the flow channels 110 of the green honeycomb molding 100 extend is not particularly limited, and may be, for example, in a range of 40 mm to 350 mm. The outer diameter of the green honeycomb molding 100 is not particularly limited, and may be, for example, in a range of 100 mm to 320 mm. In regard to the size of the cross-section of the flow channels 110, for example, in case of a square shape, one side may be in a range of 0.8 mm to 2.5 mm. The thickness of the partition walls 112 may be in a range of 0.05 mm to 0.5 mm.

The green honeycomb molding 100 is a green body (unbaked body) which becomes porous ceramics by baking later, and is a nonporous material containing a ceramics raw material. Ceramics is not particularly limited, and examples of ceramics include oxide, such as alumina, silica, mulite, cordierite, glass, or aluminum titanate, silicon carbide, silicon nitride, metal, and the like. Aluminum titanate may further contain magnesium and/or silicon.

The green honeycomb molding 100 contains, for example, inorganic compound source powder, which is a ceramics raw material, organic binder, such as methylcellulose, and additives which are added as necessary.

For example, when ceramics is aluminum titanate, inorganic compound source powder contains aluminum raw powder, such as α alumina powder, and titanium raw powder, such as anatase-type or rutile-type titania powder, and further contains magnesium raw powder, such as magnesia powder or magnesia-spinel powder, and/or silicon raw powder, such as silicon oxide powder or glass frit, as necessary.

Examples of the organic binder include celluloses, such as methylcellulose, carboxylmethylcellulose, hydroxyalkylmethylcellulose, and sodium carboxylmethylcellulose; alcohols, such as polyvinylalcohol; and lignosulfonate.

A raw mixture may contain organic additives other than the organic binder. Examples of the organic additives include a pore forming agent, a lubricant, a plasticizer, and a dispersant.

Examples of the pore forming agent include carbon materials, such as graphite, resins, such as polyethylene, polypropylene, and polymethyl methacrylate, plant materials, such as starch, nutshell, walnut shell, and cone, ice, dry ice, and the like. The addition amount of the pore forming agent is usually 0 parts by weight to 40 parts by weight with respect to 100 parts by weight of the inorganic compound powder, and is, for example, 0 parts by weight to 25 parts by weight. The pore forming agent is vanished during baking of a green molding. Accordingly, in an aluminum titanate sintered body, minute pores are formed at the points at which the pore forming agent is not present.

Examples of the lubricant and the plasticizer include alcohols, such as glycerin, higher fatty acids, such as caprylic acid, lauric acid, palmitic acid, arachic acid, oleic acid, and stearic acid, metal stearate, such as Al stearate; polyoxyalkylene alkyl ether, and the like. The addition amount of the lubricant and the plasticizer is usually 0 parts by weight to 10 parts by weight with respect to 100 parts by weight of the inorganic compound powder, and for example, 0.1 parts by weight to 5 parts by weight.

Examples of the dispersant include inorganic acids, such as nitric acid, hydrochloric acid, and sulfuric acid, organic acids, such as oxalic acid, citric acid, acetic acid, malic acid, and lactic acid, alcohols, such as methanol, ethanol, and propanol, surfactants, such as ammonium polycarboxylate, and the like. The addition amount of the dispersant is usually 0 parts by weight to 20 parts by weight with respect to 100 parts by weight of the inorganic compound powder, and is, for example, 2 parts by weight to 8 parts by weight.

As described above, the left ends of some of the plurality of flow channels 110 of the green honeycomb molding 100 are sealed by the sealing portions 114, and the right ends of the rest of the plurality of flow channels 110 of the green honeycomb molding 100 are sealed by the sealing portions 114. As the sealing portions 114, similarly to the green honeycomb molding 100, a material which becomes ceramics by baking may be used. As shown in FIG. 1(a), "some of the plurality of flow channels 110" and "the rest of the plurality of flow channels 110" respectively refer to combinations of flow channels selected for every two flow channels in the horizontal direction and the vertical direction in the plurality of flow channels arranged in a matrix when viewed from the end surface side.

The green honeycomb molding 100 can be manufactured, for example, in the following manner.

First, inorganic compound source powder, an organic binder, a solvent, and additives which are added as necessary are prepared. These are mixed by a kneader or the like to obtain a raw mixture, and the obtained raw mixture is extruded from an extruder having exit openings corresponding to the shape of the partition walls, cut to have a desired length, and dried by a known method, thereby obtaining the green honeycomb molding 100. Thereafter, the end portions of the flow channels 110 may be sealed by a known method.

Subsequently, an examination device for defects in the green honeycomb molding 100 according to the first embodiment of the invention will be described referring to FIGS. 2 and 3.

An examination device 400a includes a pressure application member 200 which applies pressure to one end (the lower end of FIG. 2) of the plurality of flow channels 110 of the green honeycomb molding 100 using gas supplied from a gas supply source 210, schlieren units 300X (first visualization unit) and 300Y (second visualization unit) as visualization units which visualize the distribution of refractive indexes of gas near the other end (the upper end of FIG. 2) of the plurality of flow channels 110, scales 360X and 360Y, an information processing device 500, and a display 600.

The pressure application member 200 has a tubular seal portion 201 which externally encircles and seals one end portion (in FIG. 2, the lower end portion) in the axial direction of the green honeycomb molding 100 (in the axial direction of the plurality of flow channels 110), and a space forming portion 202 which forms a space V in a portion facing the lower ends 110b of the plurality of flow channels 110.

A gas supply source 210 is connected to the space forming portion 202 through a line L1 having a valve V1.

Gas of the gas supply source 210 is not particularly limited insofar as gas is gas having a refractive index different from atmospheric gas near the upper ends 110t of the plurality of flow channels 110. In order to make the refractive indexes different, the density of gas may be changed. When the density of atmospheric gas (for example, air) is 1 at 0° C., 1 atm, the density of gas of the gas supply source 210 may be in a range of 0.1 to 0.9 or 1.1 to 5.0 at 0° C., 1 atm.

Specifically, for example, as gas of the gas supply source 210, gas having a composition different from atmospheric gas may be used. For example, atmospheric gas may be air from ease of examination, and when atmospheric gas is air, gas of the gas supply source 210 may be gas of one selected from a group consisting of helium, neon, nitrogen, argon, xenon, krypton, oxygen, and carbon dioxide, mixed gas (excluding an air composition) of two or more of the group, or mixed gas of one or more of the group and air. Alternatively, even when the periphery of the examination device 400a is evacuated by a method in which the periphery of the examination device 400a is closed and evacuated or an atmosphere is replaced, gas of the gas supply source 210 may be gas of one selected from a group consisting of helium, neon, nitrogen, argon, xenon, krypton, oxygen, and carbon dioxide, mixed gas (excluding an air composition) of two or more of the group, or mixed gas of one or more of the group and air. The temperature of gas of the gas supply source 210 may be in a range of 0° C. to 30° C.

Even when gas of the gas supply source 210 and atmospheric gas have the same composition, the temperature of gas of the gas supply source 210 may be different from atmospheric gas to provide a density difference in a state of being leaked into atmospheric gas, that is, a refractive index difference. In this case, a temperature difference may be in a range of 10° C. to 50° C. Of course, a difference may be provided for both the composition and the temperature.

Figure 2:
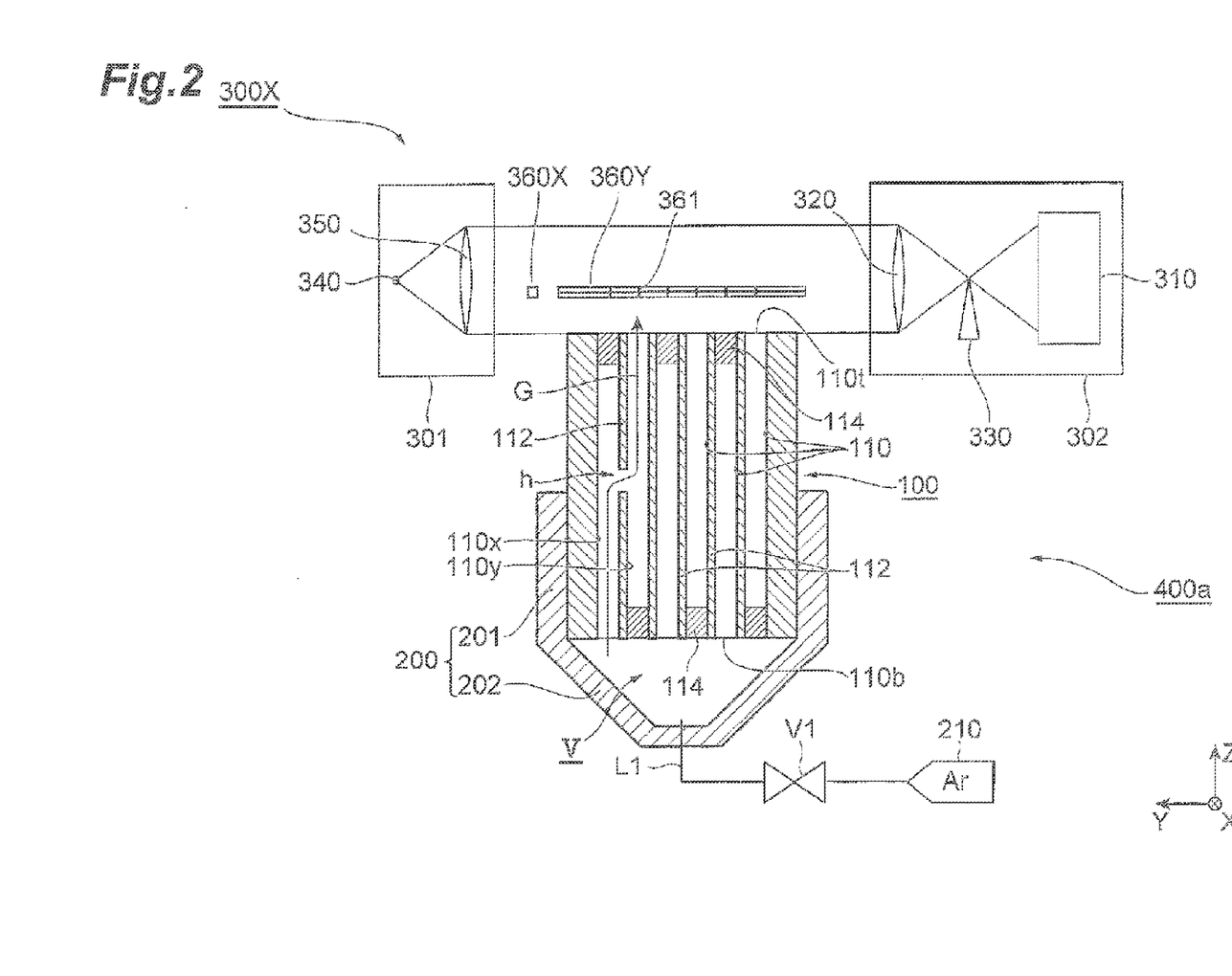
FIG. 2 is a schematic sectional view of an examination device 400a for defects in a green honeycomb molding 100 according to a first embodiment.
Figure 3:
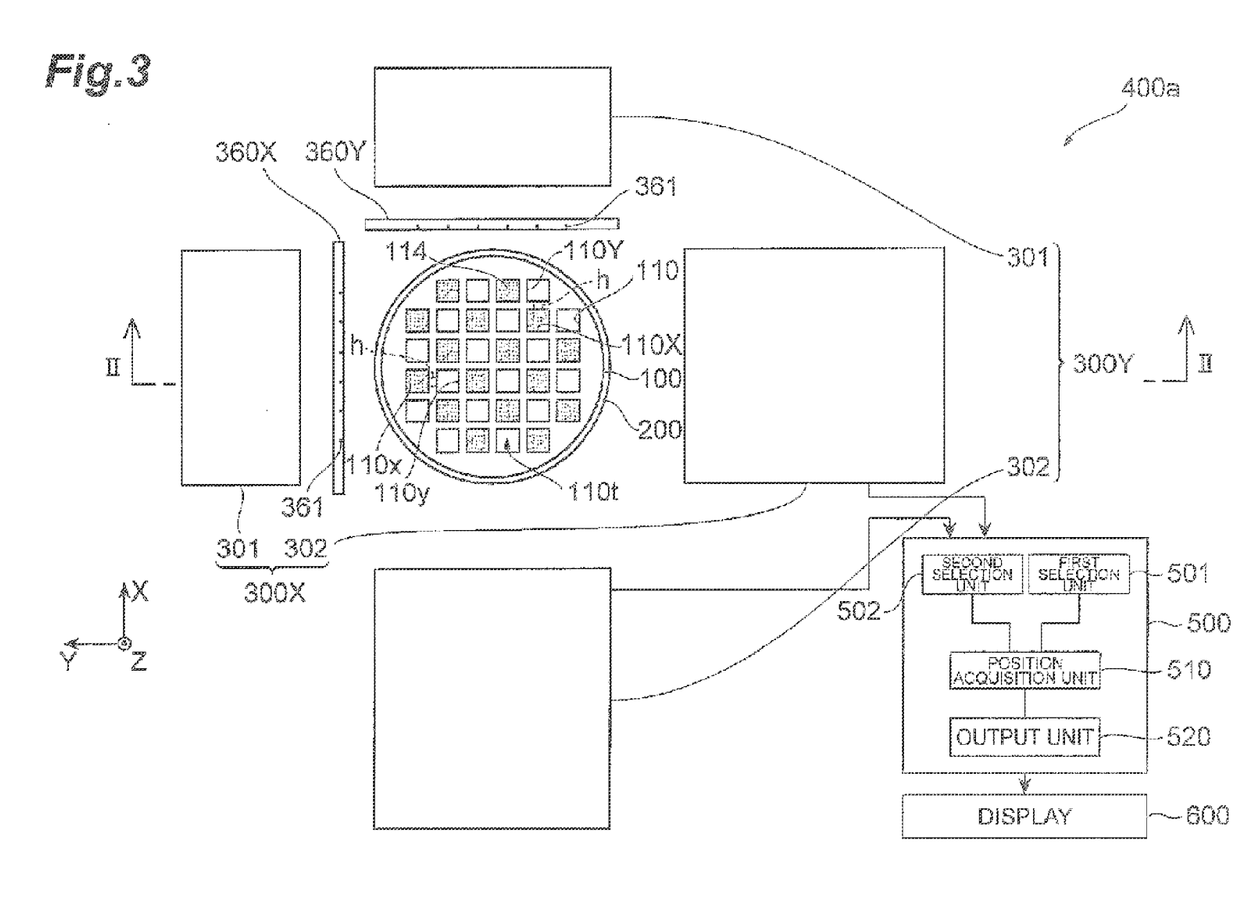
FIG. 3 is a top view of FIG. 2.

As shown in FIG. 2, the schlieren units 300X and 300Y shown in FIG. 3 acquire images visualizing the distribution of refractive indexes of gas near the upper ends 110t of the plurality of flow channels 110 of the green honeycomb molding 100, and respectively include a light source unit 301 and an observation unit 302. The light source unit 301 includes a light source 340, and a collimator lens 350 which converts light emitted from the light source 340 to parallel light. The observation unit 302 includes a collimator lens 320 which converges light emitted from the collimator lens 350 and passing over the upper ends 110t of the plurality of flow channels 110, a knife edge 330 which is provided at the focal position of converged light, and a camera 310 which photographs the image of light after passing through the knife edge 330.

In this embodiment, as shown in FIG. 3, the light source unit 301 and the observation unit 302 of the first schlieren unit 300X are separated from each other in the X direction which is a direction perpendicular to the Z direction, in which the plurality of flow channels 110 extend, and are arranged with a portion near the upper ends 110t of the plurality of flow channels 110 interposed therebetween. The light source unit 301 and the observation unit 302 of the second schlieren unit 300Y are separated from each other in the Y direction which is a direction perpendicular to the Z direction, in which the plurality of flow channels 110 extend, and are arranged with a portion near the upper ends 110t of the plurality of flow channels 110 interposed therebetween. With this, the distribution of refractive indexes of gas near the upper ends 110t of the plurality of flow channels 110 can be visualized from two directions (the X direction and the Y direction) orthogonal to the Z axis, which is the axis of the plurality of flow channels 110.

As shown in FIGS. 2 and 3, above the upper ends 110t of the plurality of flow channels 110 and close to the light source units 301 of the schlieren units 300X and 300Y, the scale 360X is arranged to be present within the visual field in which the schlieren unit 300X observes and the scale 360Y is arranged to be present within the visual field in which the schlieren unit 300Y observes. The scales 360X and 360Y respectively have marks 361 at the positions corresponding to the center axis of the plurality of flow channels 110 when viewed from the observation units 302 of the schlieren units 300X and 300Y.

The camera 302 of each of the schlieren units 300X and 300Y acquires images visualizing the density distribution regularly for each predetermined time. The predetermined time is not particularly limited, and may be, for example, in a range of 0.01 seconds to 2 seconds. The number of images to be acquired is not particularly limited, and may be, for example, in a range of 1 to 30. Each of the schlieren units 300X and 300Y can start to acquire images before gas starts to be supplied. Although the image acquisition times of the schlieren units 300X and 300Y may be synchronized, image acquisition may not be synchronized and may be carried out at different times.

As shown in FIG. 3, the information processing device 500 includes a first selection unit 501, a second selection unit 502, a position acquisition unit 510, and an output unit 520. These functions of the information processing device 500 may be realized by software which is executed on a computer.

The first selection unit 501 acquires a plurality of images acquired by the schlieren unit 300X and extracts an image having a largest number of jet flows of gas from these images. The second selection unit 502 acquires a plurality of images acquired by the schlieren unit 300Y and extracts an image having a largest number of jet flows of gas from these images.

Specifically, this step can be performed in the following manner. FIGS. 4(a) and 4(b) show two images $400X_1$ and $400X_2$ acquired by the schlieren unit 300X as an example of visualized images. FIGS. 5(a) and 5(b) show two images $400Y_1$ and $400Y_2$ acquired by the schlieren unit 300Y as an example of visualized images. The images $400X_1$ and $400Y_1$ have two jet flows D which flow out of the upper end surface of the green honeycomb molding 100, and the images $400X_2$ and $400Y_2$ have one jet flow D out of the upper end surface of the green honeycomb molding 100.

First, the images are binarized or the like to recognize the portions of the jet flows D. Next, the number of portions recognized as the portions of the jet flows D on a line parallel to the Y direction between the upper end surface of the green honeycomb molding 100 and the scale 360X is counted. This operation is performed for each image, whereby the number of jet flows D in each image acquired by the schlieren unit 300X and the number of jet flows D in each image acquired by the schlieren unit 300Y can be acquired.

Next, images having a largest number of jet flows D may be extracted from a plurality of images acquired by the schlieren unit 300X and a plurality of images acquired by the schlieren unit 300Y.

Returning to FIG. 3, the position acquisition unit 510 acquires information relating to the positions of the jet flows D in the image selected by the first selection unit 501 and the image selected by the second selection unit 502.

Figure 4:
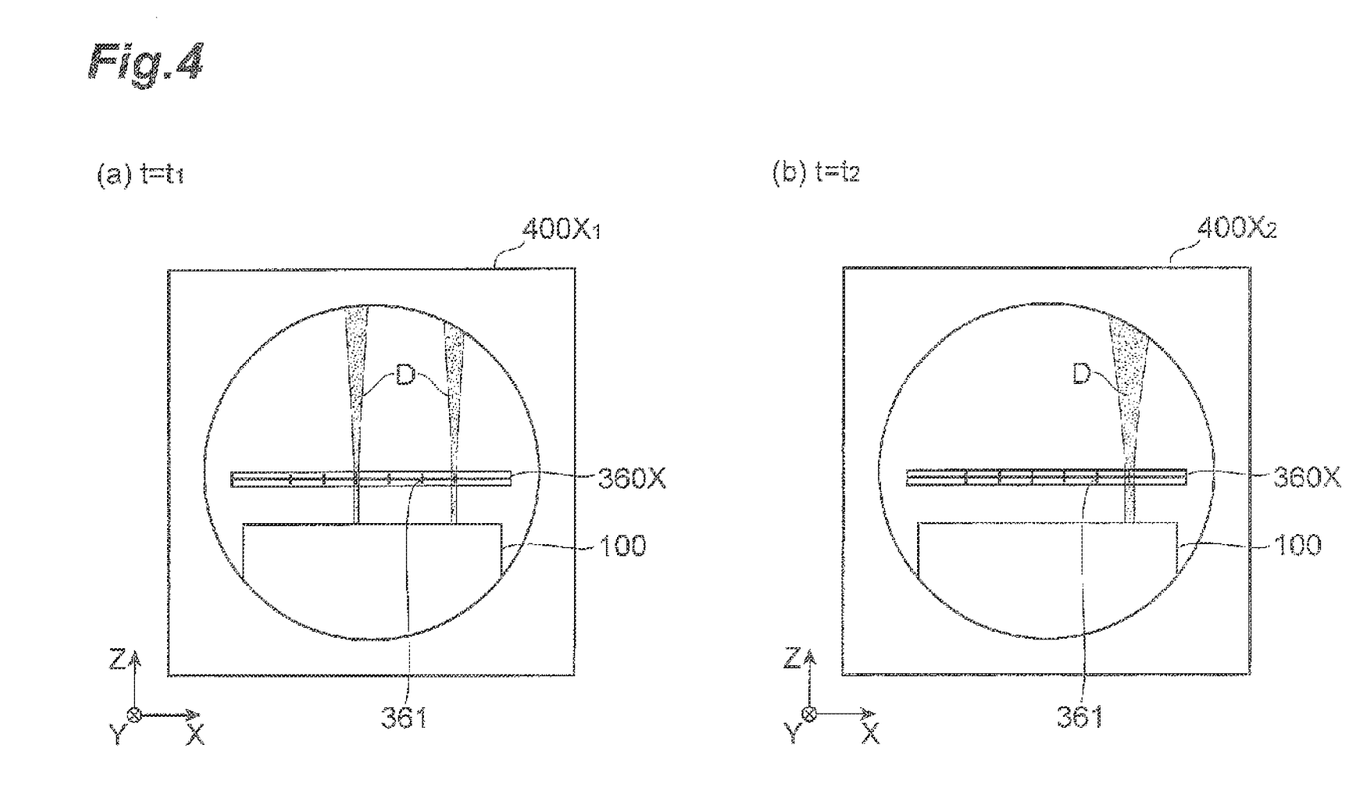
FIGS. 4(a) and 4(b) are schematic views of images $400X_1$ and $400X_2$ photographed by a camera 302 of a schlieren unit 300X at the time t=t1, t2.
Figure 5:
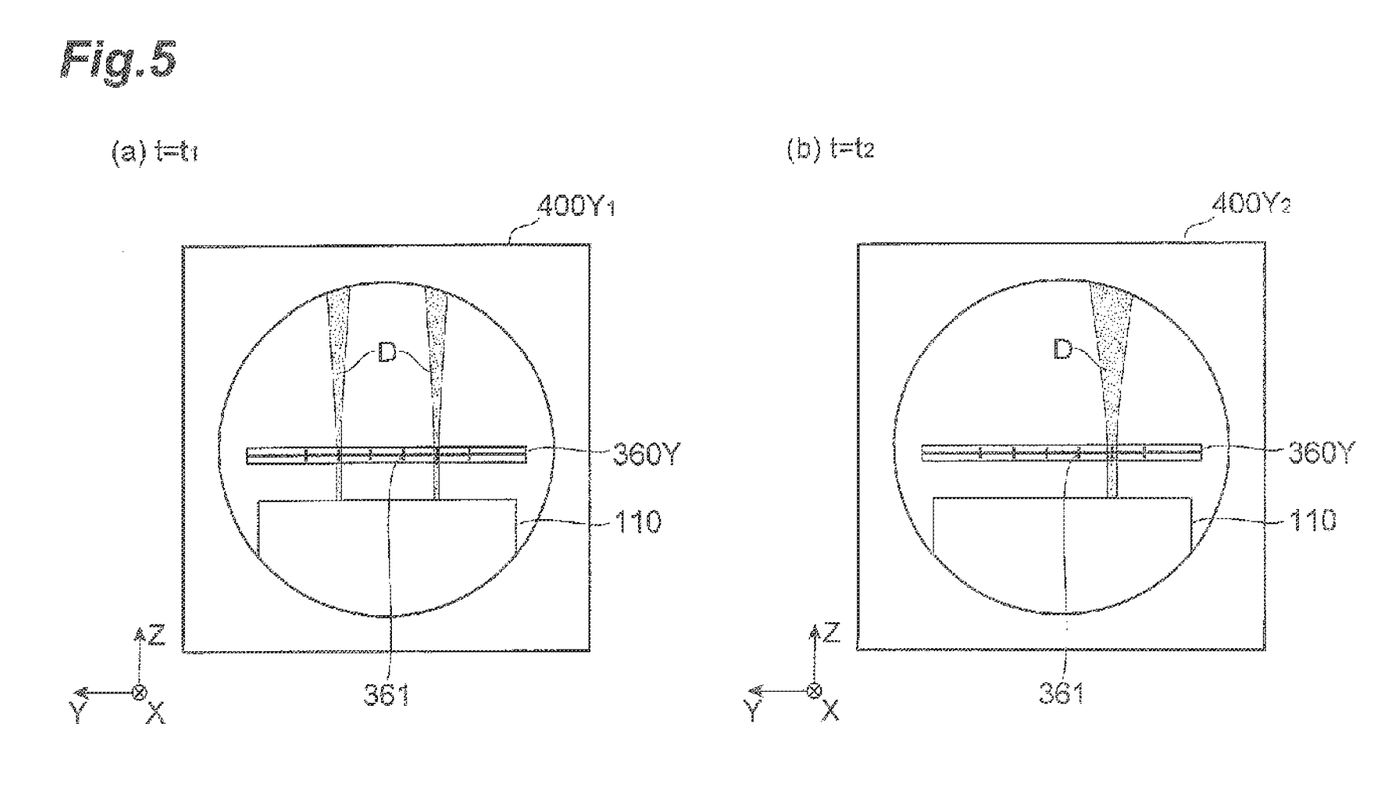
FIGS. 5(a) and 5(b) are schematic views of images $400Y_1$ and $400Y_2$ photographed by a camera 302 of a schlieren unit 400Y at the time t=t1, t2.

The acquisition method is not particularly limited, and for example, in the image $400X_1$ of FIG. 4(*a*), for example, the position of third mark in the X direction from the left and the position of the sixth mark from the left, that is, information relating to the X coordinates of 3 and 6 can be acquired based on the positions of the marks 361 of the scale 360X. For example, in the image $400Y_1$ of FIG. 5(*a*), the position of the second mark in the Y direction from the right and the position of the fifth mark from the right, that is, information relating to the X coordinates of 2 and 5 can be acquired based on the positions of the marks 361 of the scale 360Y. When there are no marks 361, the horizontal positions in the images, for example, dot numbers or the like may be used.

The output unit 520 outputs information relating to the positions of the jet flows D acquired by the position acquisition unit 510 to an output device, such as the display 600.

Subsequently, an examination method of the green honeycomb molding 100 using the above-described examination device 400 will be described.

As an example, as shown in FIG. 2, it is assumed that the partition wall 112 of the green honeycomb molding 100 has a hole h as a defect which communicates a flow channel 110*x* with a sealed upper end and a flow channel 110*y* with a sealed lower end. As shown in FIGS. 2 and 3, the flow channel 110*x* is at the position of the leftmost mark 361 in the scale 360Y and at the position of the third mark 361 from the below in the scale 360X. The flow channel 110*y* is at the position of the second mark 361 from the left in the scale 360Y and at the position of the third mark 361 from the below in the scale 360X.

First, the pressure application member 200 is mounted in the lower portion of the green honeycomb molding 100. The valve V1 is opened, and the pressure is applied to the lower ends of the plurality of flow channels 110 of the green honeycomb molding 100 using gas, for example, argon gas (a step of applying pressure). The pressure is not particularly limited, and for example, may be in a range of 0.01 MPa to 1 MPa as a differential pressure with respect to an atmospheric pressure. A state in which atmospheric gas rarely flows near the upper ends 110*t* of the plurality of flow channels 110, for example, a flow velocity is equal to or lower than 1 m/s may be set. From ease of an experiment, the temperature of atmospheric gas may be in a range of 0° C. to 30° C.

If the pressure is applied in this way, when the hole h shown in FIG. 2 is present, since a flow channel which connects the upper ends 110*t* and the lower ends 110*b* of the plurality of flow channels 110 is formed by the flow channel 110*x*, the hole h, and the flow channel 110*y*, gas G used for pressurization flows out of the upper end of the defective flow channel 110*y*. The situation is the same when there is a defect, such as missing of the sealing portion 114 or a gap between the sealing portion 114 and the flow channel 110. In contrast, when the green honeycomb molding 100 has no defect described above, even if the pressure is applied to the lower ends of the plurality of flow channels 110, gas cannot flow beyond the upper ends 110*t* of the plurality of flow channels 110, and gas does not flow over the upper ends 110*t* of the plurality of flow channels 110.

Since the refractive index of gas G is different from the refractive index of atmospheric gas near the upper ends of the plurality of flow channels 110, when there is a defect, irregularity in refractive index occurs near the upper end of the flow channel 110*y*.

Irregularity in refractive index is visualized by the schlieren units 300X and 300Y as a difference of brightness and darkness or the like and an image is acquired for each predetermined time (a step of acquiring images). FIGS. 4(*a*) and 4(*b*) are schematic views of images $400X_1$ and $400X_2$ photographed by the camera 302 of the schlieren unit 300X at the time $t=t_1$ and $t_2$. FIGS. 5(*a*) and 5(*b*) are schematic views of images $400Y_1$ and $400Y_2$ photographed by the camera 302 of the schlieren unit 300Y at the time $t=t_1$ and $t_2$.

Next, an image having a largest number of jet flows D is selected from the images $400X_n$ acquired by the schlieren unit 300X. For example, in the example of FIG. 4, since the image $400X_1$ has two jet flows D and the image $400X_2$ has one jet flow D, the image having a larger number of jet flows D from the two images is the image $400X_1$.

Similarly, an image having a largest number of jet flows D is selected from the images $400Y_n$ acquired by the schlieren unit 300Y. For example, in the example of FIG. 5, since the image $400Y_1$ has two jet flows D and the image $400Y_2$ has one jet flow D, the image having a larger number of jet flows D from the two images is the image $400Y_1$.

Subsequently, the information relating to the positions of the jet flows D is obtained for the selected images $400X_1$ and $400Y_1$. The X coordinates of the jet flows D of $400X_1$ are 3 and 6, and the Y coordinates of the jet flows D of $400Y_1$ are 2 and 5.

Since the X coordinates are two and the Y coordinates are two, potential defect positions may be narrowed down to four combinations, that is, (X,Y)=(3,2), (3,5), (6,2), and (6,5).

As shown in FIGS. 4 and 5, there is a case where the behavior of gas leakage fluctuates with time. That is, while two jet flows D are confirmed at t=t1, at t=t2, only one jet flow D is confirmed. The reason is unknown, but it is considered that the situation of internal defects varies due to circulation of gas, gas does not easily flow out of a certain defective region, and gas easily flows out of a different defective region.

While the determination about the presence/absence or the positions of actual defects may be performed manually for the potential defect positions (X,Y)=(3,2), (3,5), (6,2), and (6,5) estimated based on the images 400X and 400Y, the determination about the presence/absence or the positions of defects may be performed by a known image processing method.

According to this embodiment, irregularity in refractive index occurs near the flow channel 110*y* according to the presence/absence of a defect in the flow channel, and irregularity is visualized, thereby easily detecting the presence/absence or the locations of defects.

In this embodiment, since the distribution of refractive indexes of gas near the upper ends 110*t* of the plurality of flow channels 110 is visualized by the schlieren unit 300X and 300Y from two directions (the X direction and the Y direction) orthogonal to the axis (Z axis) of the plurality of flow channels 110, two-dimensional information (coordinate) for a location where irregularity in refractive index occurs is obtained, and a defective flow channel is easily specified. The scales 360X and 360Y are provided, whereby a defective flow channel is more easily specified.

Since it is not necessary to add particulates (for example, glycol particulates or steam mist) other than gas into gas, it is not necessary to remove particulates after examination, and the examination method is simplified.

A green honeycomb molding which is determined to be a non-defective article by this embodiment is baked by a known method, whereby a ceramics honeycomb baked body formed of a ceramics porous body is obtained. The ceramics honeycomb baked body may be used as a diesel particulate filter or the like.

Figure 6:
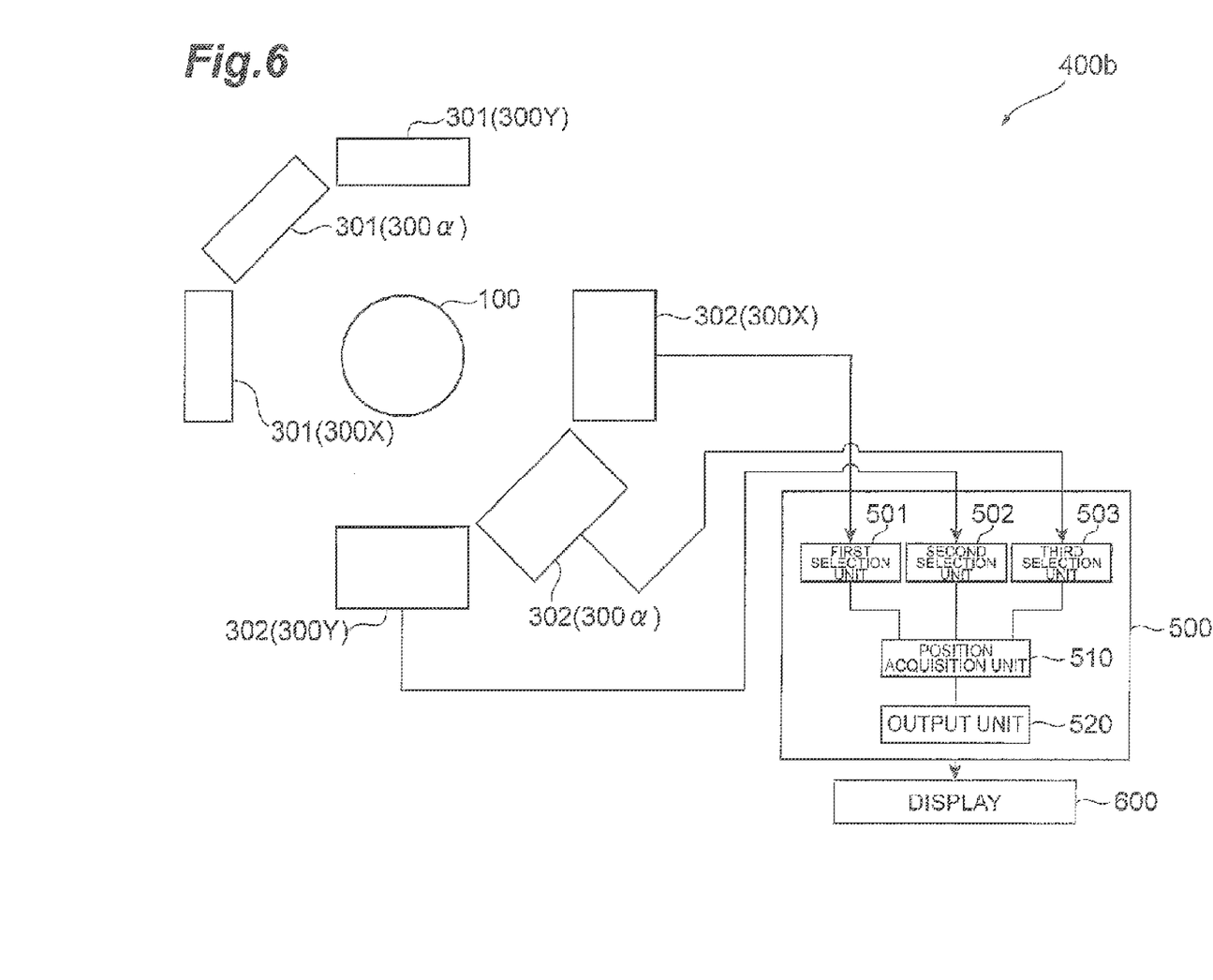
FIG. 6 is a top view of an examination device 400b for defects of a green honeycomb molding 100 according to a second embodiment.

Hereinafter, a second embodiment of the invention will be described. In an examination device 400b of this embodiment, as shown in FIG. 6, in addition to the schlieren units 300X and 300Y which can visualize the distribution of refractive indexes of gas near the upper ends 110t of the plurality of flow channels 110 from the directions of 0° and 90° as two orthogonal directions, a schlieren unit 300α which can visualize the distribution of refractive indexes of gas near the upper ends 110t of the plurality of flow channels 110 from the direction of 45° as an intermediate direction between the schlieren units 300X and 300Y. The schlieren unit 300α has the same light source unit 301 and observation unit 302 as those in the schlieren unit 300X and 300Y The same scale as the scales 360X and 360Y is arranged near the light source unit 301 of the schlieren unit 300α, but is not shown in the drawing.

The information processing device 500 includes a third selection unit 503 in addition to the first selection unit 501 and the second selection unit 502. Similarly to the first selection unit 501 and the second selection unit 502, the third selection unit 503 acquires a plurality of images acquired by the schlieren unit 300α and extracts an image having a largest number of jet flows of gas from these images.

Figure 7:
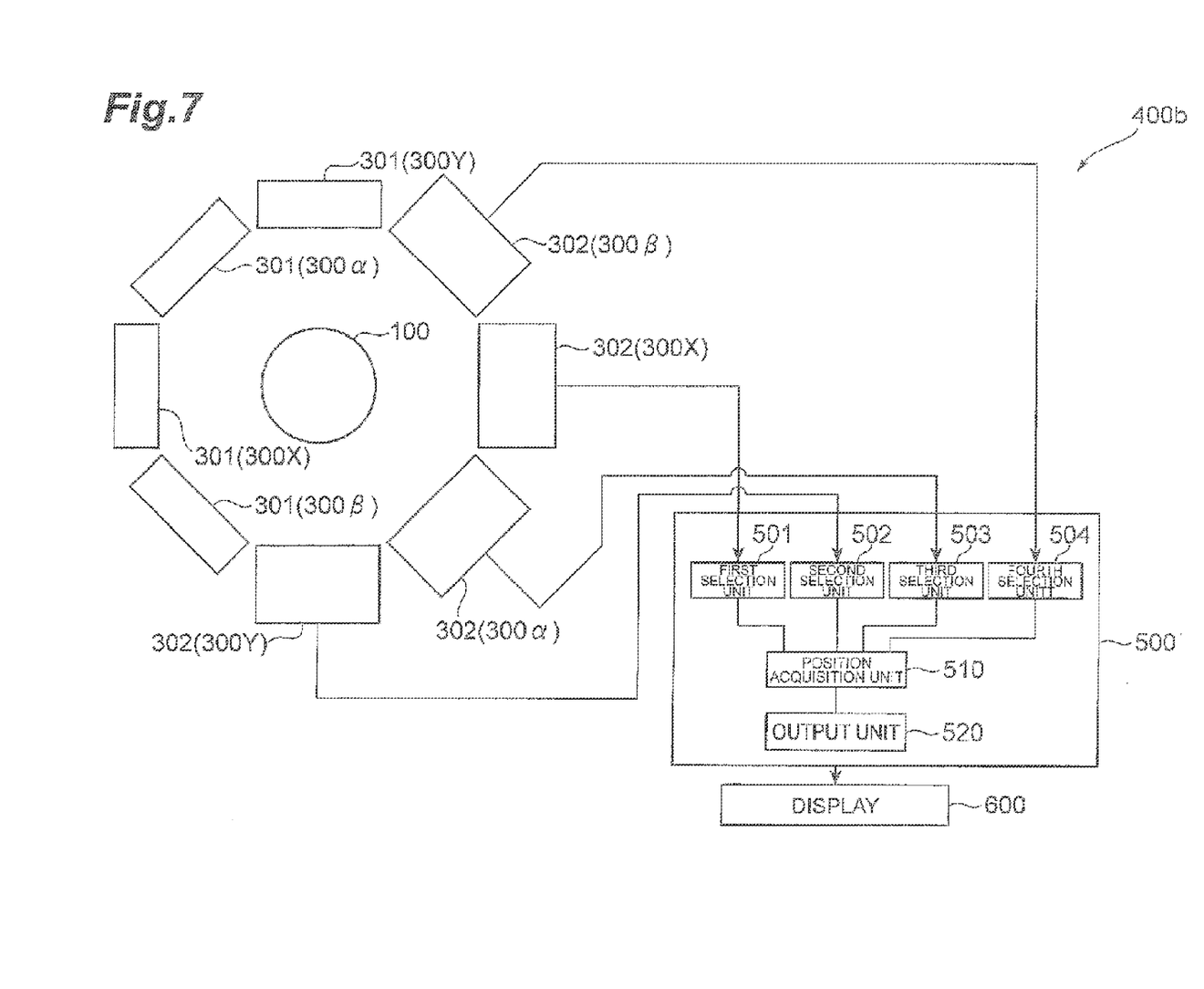
FIG. 7 is a top view showing a mode in which the number of examination directions of the examination device 400b of FIG. 6 further increases.

Alternatively, as shown in FIG. 7, the examination device 400b may include a schlieren unit 300β which, when the schlieren unit 300Y is set to 0°, can visualize the distribution of refractive indexes of gas near the upper ends 110t of the plurality of flow channels 110 from the direction 113° counterclockwise. The schlieren unit 300β has the same configuration as the schlieren units 300X, 300Y, and 300α. The schlieren units 300X to 300β may be arranged at regular intervals angularly because the positions of defects are easily specified. In this case, the information processing device 500 includes a fourth selection unit 504 in addition to the first selection unit 501, the second selection unit 502, and the third selection unit 503. Similarly to the first selection unit 501 to the third selection unit 503, the fourth selection unit 504 acquires a plurality of images acquired by the schlieren unit 300β and extracts an image having a largest number of jet flows of gas from these images.

Hereinafter, the operation of the examination device 400b of this embodiment will be described. Similarly to the examination device 400a of the first embodiment, the examination device 400b first visualizes the distribution of refractive indexes of gas near the upper ends 110t of the plurality of flow channels 110 from two directions by the schlieren units 300X and 300Y. At this time, when the number of combinations of positions where defects are likely to be present is equal to or greater than a predetermined threshold value, for example, five, the examination device 400b visualizes the distribution of refractive indexes of gas near the upper ends 110t of the plurality of flow channels 110 from three directions including the schlieren unit 300α. The number of examination directions increases, thereby further limiting the combinations of the positions where defects are likely to be present.

With the examinations from the three directions, when the number of combinations of the positions where defects are likely to be present is less than the predetermined threshold value, as in the above-described first embodiment, the determination about the presence/absence or the positions of defects is performed manually or by a known image processing method. When it is not yet possible to specify that the number of combinations of the positions where defects are likely to be present is less than the predetermined threshold value, the examination device 400b visualizes the distribution of refractive indexes of gas near the upper ends 110t of the plurality of flow channels 110 from four directions including the schlieren unit 300β.

In this embodiment, additional schlieren units may be provided, and examinations from five or more directions may be performed. In this embodiment, an examination direction may be increased in a stepwise manner until it is possible to specify that the number of combinations of the positions where defects are likely to be present is less than the predetermined threshold value. In this embodiment, examination may be performed using all schlieren units arranged at a time.

In this embodiment, when it is estimated that the number of positions where defects are likely to be present is equal to or greater than a predetermined threshold value by information relating to the positions of the jet flows in the two images of the X direction and the Y direction, similarly, a plurality of images visualizing the distribution of refractive indexes of gas are acquired from three or more directions at different times, images having a largest number of jet flows of gas discharged from the other end of the plurality of flow channels is selected from the three or more direction images, and information relating to the positions of the jet flows in the selected three or more images is acquired. With this, it is possible to acquire information relating to the positions of the jet flows in a larger number of images, and to limit the positions, at which defects are likely to be present, to a smaller number of positions.

Figure 8:
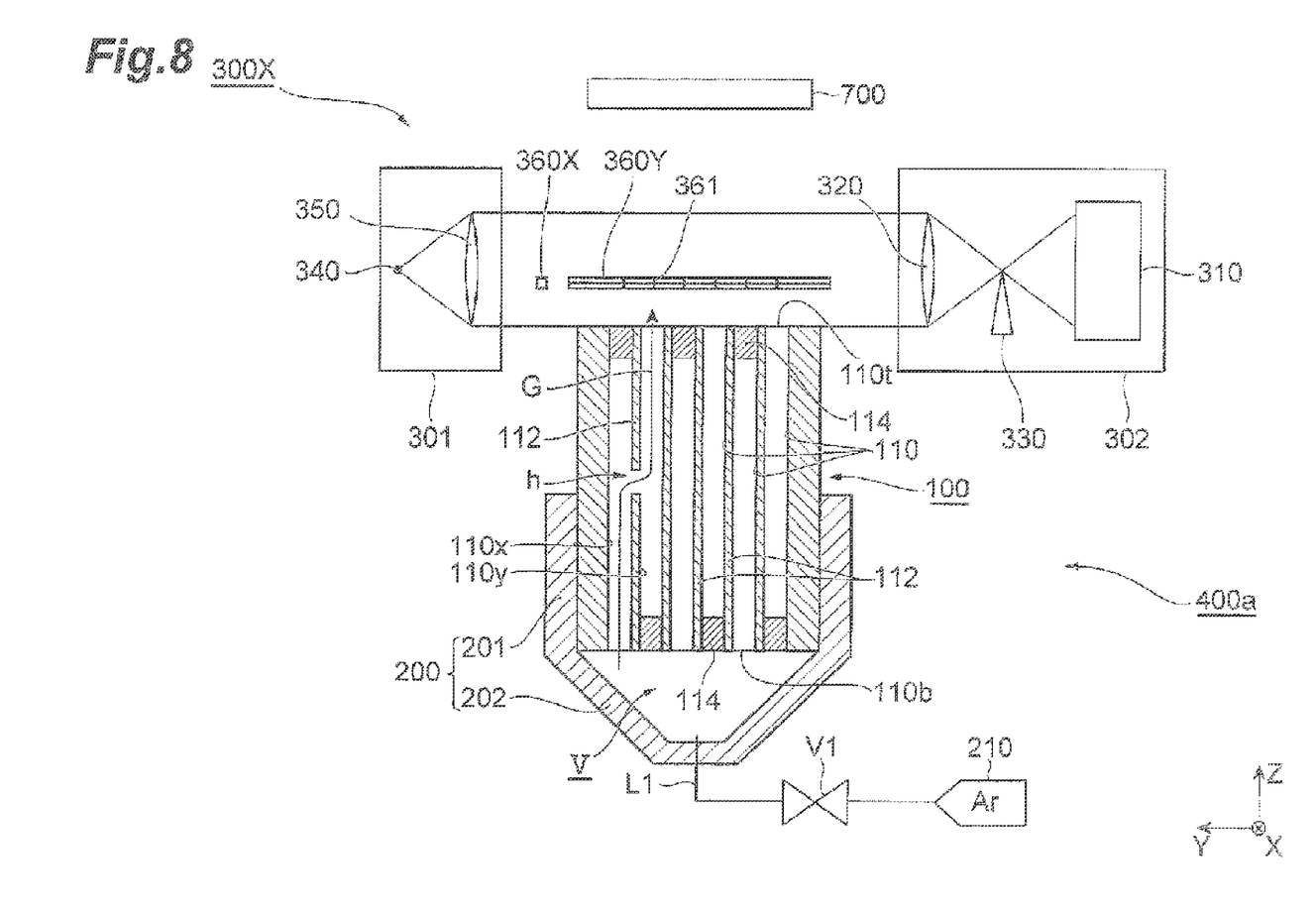
FIG. 8 is a schematic sectional view of an examination device 400c for defects in a green honeycomb molding 100 according to a third embodiment.

Hereinafter, a third embodiment of the invention will be described. As shown in FIG. 8, in an examination device 400c of this embodiment, a pressure sensor 700 is arranged near the upper ends 110t of the plurality of flow channels 110. The pressure sensor 700 divides the upper ends 110t of the plurality of flow channels 110 in a matrix and detects the pressure of jet flows D from these divisions. The position acquisition unit 510 of the information processing device 500 acquires the positions of the jet flows D based on the detection result of the pressure sensor 700.

According to this embodiment, since the pressure of the jet flows D of gas discharged from the upper ends 110t of the plurality of flow channels 110 is detected to acquire information relating to the positions of the jet flows D, it is possible to limit the positions, at which defects are present, with higher precision.

The invention is not limited to the above-described embodiments, and various modifications may be made.

For example, in the above-described embodiments, although the schlieren method is used as the method of visualizing the distribution of refractive indexes, the invention is not limited thereto insofar as the refractive index difference of gas can be visualized, and for example, a shadow graph method or a Mach-Zehnder method may be used.

In the above-described embodiment, although the two schlieren units 300X and 300Y are provided, even if only one schlieren unit is provided, the determination about the presence/absence of defects is possible, and the positions of defects can be understood roughly.

In the above-described embodiments, although atmospheric gas is air, it is needless to say that other kinds of gas may be used as atmospheric gas.

In the above-described embodiments, although the flow channels 110 of the green honeycomb molding 100 are arranged in the up-down direction, arrangement may be carried out in any direction.

In the above-described embodiments, although the cross-sectional shape of the flow channels 110 is substantially a square shape, the invention is not limited thereto, and a rectangular shape, a circular shape, an elliptical shape, a triangular shape, a hexagonal shape, an octagonal shape, or the like may be used. In the flow channels 110, flow channels having different diameters or flow channels having different cross-sectional shapes may be mixed. Although the arrangement of the flow channels is square arrangement in FIG. 1, the invention is not limited thereto, and regular triangular arrangement in which the center axis of a flow channel is arranged at the vertex of a regular triangle in a cross-section, zigzag arrangement, or the like may be used. The outer shape of the green honeycomb molding is not limited to a column, and for example, a triangular prism, a quadrangular prism, a hexagonal prism, an octagonal prism, or the like may be used,

INDUSTRIAL APPLICABILITY

According to the embodiment of the invention, it is possible to easily examine defects in a green honeycomb molding.

REFERENCE SIGNS LIST

100: green honeycomb molding
110: flow channel
110t: upper end (one end) of flow channel
110b: lower end (the other end) of flow channel
112: partition wall
114: sealing portion
200: pressure application member
300X, 300Y, 300α, 300β: schlieren unit
360: scale
400a, 400b, 400c: examination device
500: information processing device
501: first selection unit
502: second selection unit
503: third selection unit
504: fourth selection unit
510: position acquisition unit
520: output unit
600: display
700: pressure sensor

The invention claimed is:

1. A method of examining defects in a green honeycomb molding having partition walls which form a plurality of flow channels extending in parallel with one another, and sealing portions which close one end of some of the plurality of flow channels and the other end of the rest of the plurality of flow channels, the method comprising:
   a step of applying pressure to one end of the plurality of flow channels using gas;
   a step of acquiring a plurality of first direction images visualizing the distribution of refractive indexes of gas near the other end of the plurality of flow channels from a first direction intersecting the axis of the plurality of flow channels at different times;
   a step of acquiring a plurality of second direction images visualizing the distribution of refractive indexes of gas near the other end of the plurality of flow channels from a second direction intersecting the axis of the plurality of flow channels and intersecting the first direction at different times;
   a step of selecting an image having a largest number of jet flows of gas discharged from the other end of the plurality of flow channels of the green honeycomb molding in the plurality of first direction images;
   a step of selecting an image having a largest number of jet flows of gas discharged from the other end of the plurality of flow channels of the green honeycomb molding in the plurality of second direction images; and
   a step of acquiring information relating to the positions of the jet flows in the selected two images.

2. The method according to claim 1, further comprising:
when the number of positions where defects in the green honeycomb molding are likely to be present by information acquired in the step of acquiring information relating to the positions of the jet flows in the selected two images is equal to or greater than a predetermined threshold value,
a step of acquiring a plurality of third to nth direction images visualizing the distribution of refractive indexes of gas near the other end of the plurality of flow channels from third to n-th directions (where n is an integer equal to or greater than 3) intersecting the axis of the plurality of flow channels, intersecting the first direction and the second direction, and intersecting one another at different times;
a step of selecting images having a largest number of jet flows of gas discharged from the other end of the plurality of flow channels of the green honeycomb molding in the third to n-th direction images; and
a step of acquiring information relating to the positions of the jet flows in the selected three to n images.

3. The method according to claim 1, further comprising:
a step of detecting the pressure of the jet flows of gas discharged from the other end of the plurality of flow channels of the green honeycomb molding to acquire information relating to the positions of the jet flows.

4. The method according to claim 1,
wherein the distribution of refractive indexes is visualized by one of a shadow graph method, a Mach-Zehnder method, and a schlieren method.

5. The method according to claim 1,
wherein, when the density of atmospheric gas near the other end of the plurality of flow channels is 1 at 0° C., 1 atm, the density of gas for applying the pressure is in a range of 0.1 to 0.9 or 1.1 to 5.0 at 0° C., 1 atm.

6. The method according to claim 1,
wherein the pressure is applied to one end of the plurality of flow channels using gas having a composition different from atmospheric gas near the other end of the plurality of flow channels.

7. The method according to claim 6,
wherein, in either a state in which the vicinity of the other end of the plurality of flow channels is in vacuum or a state in which atmospheric gas near the other end of the plurality of flow channels is gas having a density difference from gas for applying the pressure, gas for applying the pressure is gas of one selected from a group consisting of helium, neon, nitrogen, argon, xenon, krypton, oxygen, and carbon dioxide, mixed gas of two or more of the group, or mixed gas of one or more of the group and air.

8. The method according to claim 1,
wherein the pressure is applied to one end of the plurality of flow channels using gas at a temperature different from atmospheric gas near the other end of the plurality of flow channels.

9. The method according to claim 1,
wherein scales are arranged within the visual field of the first direction images and the second direction images.

10. A method of manufacturing a green honeycomb structure, the method comprising:
a step of recognizing the positions of defects based on the method of examining defects in a green honeycomb molding according to claim 1; and
a step of repairing the recognized defects.

11. A device for examining defects in a green honeycomb molding having partition walls which form a plurality of flow channels extending in parallel with one another, and sealing portions which close one end of some of the plurality of flow channels and the other end of the rest of the plurality of flow channels, the device comprising:
a pressure application member which applies pressure to one end of the plurality of flow channels using gas supplied from a gas supply source;
a first visualization unit which acquires a plurality of first direction images visualizing the distribution of refractive indexes of gas near the other end of the plurality of flow channels from a first direction intersecting the axis of the plurality of flow channels at different times;
a second visualization unit which acquires a plurality of second direction images visualizing the distribution of refractive indexes of gas near the other end of the plurality of flow channels from a second direction intersecting the axis of the plurality of flow channels and intersecting the first direction at different times;
a first selection unit which selects an image having a largest number of jet flows of gas discharged from the other end of the plurality of flow channels of the green honeycomb molding in the plurality of first direction images;
a second selection unit which selects an image having a largest number of jet flows of gas discharged from the other end of the plurality of flow channels of the green honeycomb molding in the plurality of second direction images; and
a position acquisition unit which acquires information relating to the positions of the jet flows in the selected two images.

12. The device according to claim 11, further comprising:
when the number of positions where defects in the green honeycomb molding are likely to be present by information acquired by information relating to the positions of the jet flows in the selected two images acquired by the position acquisition unit is equal to or greater than a predetermined threshold value,
a third visualization unit to an n-th visualization unit which acquire a plurality of third to n-th direction images visualizing the distribution of refractive indexes of gas near the other end of the plurality of flow channels from third to n-th directions (where n is an integer equal to or greater than 3) intersecting the axis of the plurality of flow channels, intersecting the first direction and the second direction, and intersecting one another at different times; and
a third selection unit to an n-th selection unit which select images having a largest number of jet flows of gas discharged from the other end of the plurality of flow channels of the green honeycomb molding in the third to n-th direction images,
wherein the position acquisition unit acquires information relating to the positions of the jet flows in the selected three to n images.

13. The device according to claim 11, further comprising:
a pressure sensor which detects the pressure of the jet flows of gas discharged from the other end of the plurality of flow channels of the green honeycomb molding,
wherein the position acquisition unit acquires information relating to the positions of the jet flows by the pressure of the jet flows of gas discharged from the other end of the plurality of flow channels detected by the pressure sensor.

* * * * *